United States Patent [19]

O'Bear et al.

[11] Patent Number: 5,932,177

[45] Date of Patent: Aug. 3, 1999

[54] TEST SAMPLE CARD

[75] Inventors: Raymond E. O'Bear, Granite City, Ill.;
Bruno Colin, Marcy L'Etoile, France;
G. R. Tegeler, Hazelwood; John L. Staples, Florissant, both of Mo.

[73] Assignee: bio Merieux, Inc., Hazelwood, Mo.

[21] Appl. No.: 08/872,812

[22] Filed: Jun. 11, 1997

Related U.S. Application Data

[62] Division of application No. 08/681,310, Jul. 22, 1996, Pat. No. 5,869,005, which is a division of application No. 08/455,534, May 31, 1995, Pat. No. 5,609,828.

[51] Int. Cl.⁶ .................................................... C12M 1/18
[52] U.S. Cl. .................................. 422/102; 435/288.4
[58] Field of Search ................. 422/99–104; 435/288.4, 435/305.3

[56] References Cited

U.S. PATENT DOCUMENTS

| | | |
|---|---|---|
| D. 243,542 | 3/1977 | Fadler et al. . |
| D. 243,543 | 3/1977 | Fadler et al. . |
| 3,963,355 | 6/1976 | Aldridge et al. . |
| 4,018,652 | 4/1977 | Lanham et al. . |
| 4,038,151 | 7/1977 | Fadler et al. . |
| 4,116,775 | 9/1978 | Charles et al. . |
| 4,159,875 | 7/1979 | Hauser . |
| 4,188,280 | 2/1980 | Charles et al. . |
| 4,207,394 | 6/1980 | Aldridge, Jr. et al. . |
| 4,318,994 | 3/1982 | Meyer et al. . |
| 4,395,125 | 7/1983 | Kaneko et al. . |
| 4,806,316 | 2/1989 | Johnson et al. . |
| 4,818,493 | 4/1989 | Coville et al. . |
| 4,912,744 | 3/1990 | Blood et al. .............................. 379/6 |
| 5,168,766 | 12/1992 | Stoffel . |
| 5,230,866 | 7/1993 | Shartle et al. . |
| 5,340,747 | 8/1994 | Eden . |
| 5,374,395 | 12/1974 | Robinson et al. . |
| 5,589,350 | 12/1996 | Bochner . |

FOREIGN PATENT DOCUMENTS

| | | |
|---|---|---|
| 107631 | 5/1984 | European Pat. Off. . |
| 282 840 | 9/1988 | European Pat. Off. . |
| 445 053 | 9/1991 | European Pat. Off. . |
| 2368774 | 5/1978 | France . |
| 2025611 | 1/1980 | United Kingdom . |
| WO 83/03677 | 10/1983 | WIPO . |
| WO 94/11489 | 5/1994 | WIPO . |

*Primary Examiner*—Lyle A. Alexander
*Attorney, Agent, or Firm*—McDonnell Boehnen Hulbert & Berghoff

[57] ABSTRACT

An improved sample card is provided. The improved card, typically used in biochemical analysis, achieves high sample well capacity and improved fluid flow, including by means of a plurality of through-channels which route the fluid flow of samples along both the front and back surfaces of the card. Elevated bubble traps are provided, as are integral interrupt slots for sensing card position and alignment. A bezeled leading edge facilitates insertion.

6 Claims, 4 Drawing Sheets

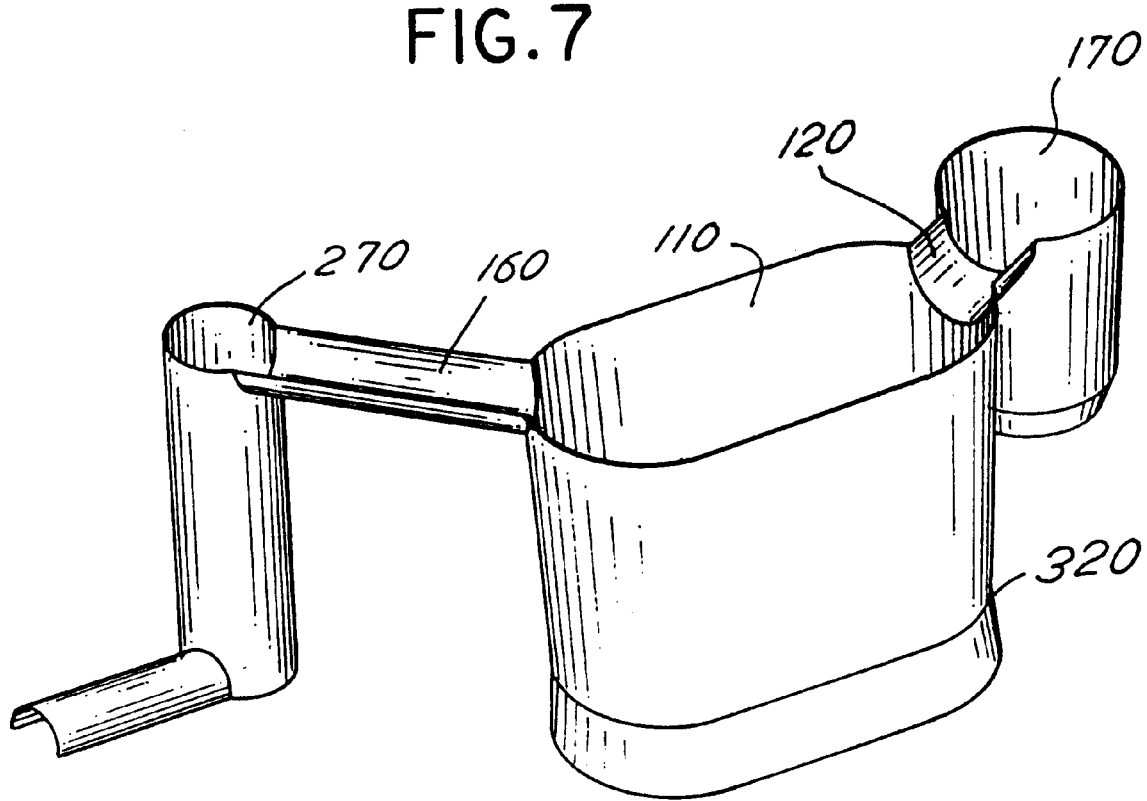

TEST SAMPLE CARD

This is a divisional of application Ser. No. 08/681,310, filed Jul. 22, 1996, now U.S. Pat. No. 5,869,005 which is a divisional of application 08/455,534 filed May 31, 1995, now U.S. Pat. No. 5,609,828.

FIELD OF THE INVENTION

The invention relates to an improved sample card for analyzing biological or other samples.

BACKGROUND OF THE INVENTION

Biocards have been used to analyze blood or other biological samples in a spectroscopic or other automated reading machine. Such machines receive a small biocard, roughly the size of a playing card, in which biological reagents, nutrients or other material is deposited and sealed, prior to injection of patient samples.

The biocard contains the reagents and receives the patient samples in a series of small wells, formed in the card in rows and columns and sealed, typically with tape on both sides. The biocards are filled with patient sample material through fine hydraulic channels formed in the card. The microorganisms in the samples may then be permitted to grow or reactions to proceed, generally over a period of up to a few hours, although the period varies with the type of bacteria or other substance analyzed and sample used.

After the incubation, the samples contained in the wells are placed in front of a laser, fluorescent light or other illumination source. The content of the sample in a given well can then be deduced according to readings on the spectrum, intensity or other characteristics of the transmitted or reflected radiation, since the culture of different bacteria or other agents leave distinctive signatures related to turbidity, density, byproducts, coloration, fluorescence and so forth. Biocards and machines for reading them of this general type for use in these biochemical applications can for example be seen in U.S. Pat. Nos. 4,318,994; 4,118,280; 4,116,775; 4,038,151; 4,018,652; and 3,957,583.

Despite the general success of biocards in this area, there is an ongoing desire to improve the performance of the cards and readings on their samples. It is for example an advantage to impress more reaction wells in a given card, so that a greater variety of reactions and therefore discrimination of samples can be realized. A given facility may have only one such machine, or be pressed for continuous analysis of samples of many patients, as at a large hospital. Conducting as many identifying reactions on each sample as possible is frequently desirable, yielding greater overall throughput.

However, biocards that have been exploited commercially have often been limited to a total of 30 sample wells (or 45 wells in some designs). For compatibility with existing reading machines, the cards generally can not be enlarged from a certain standard profile (roughly 3½" by 2¼"). Total well capacity has accordingly not grown beyond these levels, limiting the throughput on the machines.

It has also been the case that as the total number of reaction wells on a given card has increased, while the card size has remained constant, the wells have necessarily been formed increasingly close together. With the sample wells crowding each other on the card, it has become more likely that the sample contained in one well can travel to the next well, to contaminate the second well. The threat of increased contamination comes into play especially as card well capacity increases above 30 wells.

SUMMARY OF THE INVENTION

It is accordingly an object of the invention to provide a biocard having an increased number of sample wells.

It is another object of the invention to provide a biocard with increased capacity, yet retaining overall standard card sizes.

It is another object of the invention to provide a biocard which can be loaded with samples quickly, easily and with a minimum of sample corruption.

It is another object of the invention to provide a biocard with improved disposal of injection bubbles arising during loading of the samples.

It is another object of the invention to provide a biocard which increase the effective fluid flow distance between adjacent wells, reducing well-to-well contamination.

It is another object of the invention to provide a biocard with better, smoother, more reliable fluid flow throughout the card.

The invention achieving these and other objects is an improved biocard having a significantly improved sample well capacity, easily achieving 45 wells, and reaching 64 wells and feasibly more. The biocard of the invention likewise provides carefully structured fluid channels which improve fluid flow, reduce bubbling yet improve disposal of any bubbles which do form through specially designed bubble traps.

The biocard of the invention provides, as well, improved security against well-to-well contamination, in part by increasing the effective distance that the samples in adjacent sample wells must travel to corrupt neighboring sites.

BRIEF DESCRIPTION OF THE DRAWINGS

The invention will be described with reference to the drawings, in which like parts are labelled with like numbers. The drawings are briefly described below.

FIG. 7 illustrates a sample well with associated fill channel and bubble trap, according to the improved biocard to the invention.

DETAILED DESCRIPTION OF THE DRAWINGS

Figure 1:
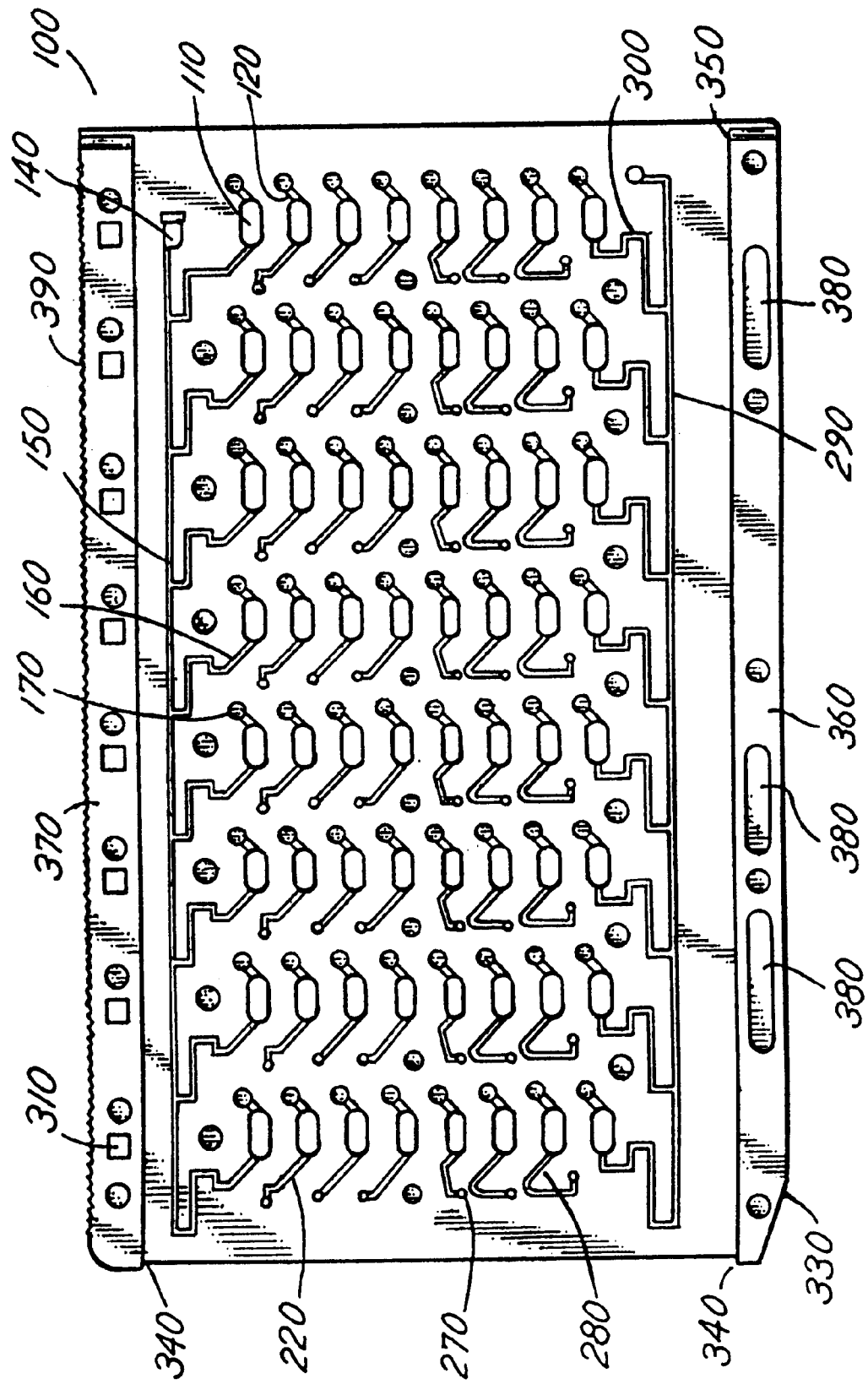
FIG. 1 illustrates an improved biocard according to the invention, in a front planar view.

A preferred embodiment of the invention is illustrated in FIGS. 1–7. This embodiment provides an improved biocard 100, having a generally rectangular shape and in standard dimensions. Biocard 100 in the illustrated embodiment contains a total of 64 separate sample wells 110, each of which receives a sample, for example a biological sample extracted from blood, other fluids, tissue or other material of a patient, for spectroscopic or other automated analysis. The biological sample may be a direct sample from the patient, or be patient sample which is extracted, diluted, suspended, or otherwise treated, in solution or otherwise. Other types of samples, including antibiotic dosages or other material, can also be introduced for analysis. It will be understood that well capacities other than 64 can be used. Biocard 100 is generally used in a landscape orientation.

In terms of materials, biocard 100 may be made of polystyrene, PET, or any other suitable plastic or other material. Biocard 100 may be tempered during manufacture with a softening material, so that crystalline rigidity, and resultant tendency to crack or chip, is reduced. Biocard 100 for instance may be manufactured out of a blend of polystyrene, approximately 90% or more, along with an additive of butyl rubber to render the card slightly more flexible and resistant to damage. Biocard 100 may also be doped with coloring agents, for instance titanium oxide to produce a white color, when desired.

The biocard 100 of the invention may be of use in identifying and/or enumerating any number of microorganisms, such as bacterial and/or other biological agents. Many bacteria lend themselves to automated spectroscopic, fluorescent and similar analysis after incubation, as is known in the art. The transmission and absorption of light is affected by the turbidity, density and colormetric properties of the sample. Fluorescent reactions may be performed as well, independently or along with spectroscopic or other measurements. If fluorescent data are gathered, use of a coloring agent in biocard 100 is preferable, since an opaque card reduces or eliminates the scattering of fluorescent emissions throughout the card, as can occur with a translucent material. Other types of detection and analysis can be done on biocard 100, including testing of susceptibility of microorganisms to antibiotics of different types, and at different concentrations, so that biocard 100 is a general-purpose instrument.

To receive sample fluid, the biocard 100 includes a sample intake plenum or port 120 at an upper right corner of the card 100, located on a perimeter edge of the card. The sample wells of card 100 contain dry biological reagents which are previously put in place in the wells, by evaporative, freeze-drying or other means, prior to being dissolved in solution with the injected patient sample for analysis. Each well can hold a deposit of a different reagent, for identifying different biological agents, if desired.

Intake port 120 receives a fluid injection tip and related assembly (schematically illustrated as 130), through which the sample fluid or other solution which arrives to dissolve the biological reagent is injected, under a vacuum pulled on biocard 100 (typically 0.7–0.9 PSIA), then released to atmospheric pressure. Injection port 120 includes a small intake reservoir 140 formed as a roughly rectangular hole through the card 100, which receives incoming fluid, and acts as a fluid buffer.

The fluid (patient sample or other solution) enters intake port 120, collects in intake reservoir 140 and travels along first distribution channel 150, located on the front or facing side of card 100. First distribution channel 150 consists of a relatively long channel formed in the surface of card 100, which extends substantially across the width of the card, and may have a cross section of approximately 0.1–0.2 mm$^2$. First distribution channel 150 is tapped at intervals along its length by a series of parallel distribution legs or fill channels 160, which generally descend from channel 150 toward the sample wells 110 in each of the eight illustrated columns. When the sample is injected into the card, a short segment of the sample tip can be pinched off or heat sealed and left in place in intake port 120, acting as a sealing plug.

Fill channels 160 are relatively short channels (which may be kinked) which extend down from first distribution channel 140 into respective sample wells 110 located in the first row of card 100, and having a cross section of approximately 0.1–0.2 mm$^2$.

It will be appreciated that each of fill channels 160 descend to and enter sample wells 110 at an angle, which results in the natural flow of the sample fluid down through the fill channels 160 by gravity, and resistance to small pieces of undissolved material flowing back up into the fluid circuitry. When the sample fluid actually enters the well 110, the fluid fills the well by action of both gravity and a vortex-type of flow effect into that well. Also, any of the fill channels 160, as schematically illustrated in FIG. 7, as well as other connecting fluid channels in the invention may be preferably formed in full-radius style, that is, as a semicircular conduit, rather than a squared-off channel as in some older designs. The full-radius feature has been found by the inventors to reduce friction and fluid turbulence, further enhancing the performance of biocard 100.

Each of sample wells 110 in the first and other rows includes an associated bubble trap 170, connected to sample well 110 at an upper corner of the well, and located at a height slightly above the well on the card surface. As illustrated in FIG. 7, each bubble trap 170 is connected to its respective well by a short trap connecting conduit 180, formed as a hollow passage part-way into the card surface and forming a short conducting path for trapped gaseous bubbles which have been formed in, or communicated to, the well 110 during the injection operation, by bacterial or other biological reaction, or otherwise. Bubble trap 170 does not cut through the card completely, instead consisting of a depression or well of roughly cylindrical shape, with a rounded bottom contour, and a volume of approximately 4.2 cubic mm in the illustrated embodiment.

Because the bubble trap 170 is located at an elevated position above each respective well 110, any gaseous bubbles will tend to rise and be trapped in the depression of trap 170. With gaseous remnants led off to the bubble trap 170, analytical readings on the biological sample can be made more reliably, since scattering and other corruption of the microbial radiation reading by gas is reduced or eliminated.

As will also be understood from the following, the two-sided nature of biocard 100 permits fluid channels to be formed opposite to non-penetrating bubble traps 170, on the other side of the card. Some older card designs have employed bubble traps which penetrate through the card, eliminating the possibility of surface channels being routed in their vicinity.

In addition to the introduction of fluid through the path of first distribution channel 150, fluid also travels to wells below the first row of wells through other directions. More specifically, intake port 120 also connects to a second distribution channel 190 formed on the opposite or back surface of the biocard 100, second distribution channel 190 also leading away from the intake reservoir 140. Second distribution channel 190 also extends substantially along the width of card 100, but on the rear surface of the card. Second distribution channel 190 has a cross-sectional area of approximately 0.2–0.3 mm$^2$.

Second distribution channel 190 is tapped above each of the eight illustrated columns of sample wells by a triplet of additional distribution legs or channels 200. Each of triplet legs 200 contains three relatively short connecting channels leading down from second distribution channel to a set of three respective through-channels 210 formed through the body of card 100.

Through-channels 210 are small apertures, approximately 1 mm in diameter, formed cleanly through the body of biocard 100, forming conduits or vias from one surface of the card to the other. The channels of triplet legs 200 connect to the respective through-channels 210, which in turn are connected to additional well fill channels 220, forming a short link to three additional respective samples wells 110.

However, the fill channels 220 deliver the fluid to the sample wells from the opposite, that is rear, side of the card 100, creating a different fluid flow circuit which extends from intake port 120. That is, this path involves the second distribution channel on the rear surface of the card, through the body of the card by way of through-channels 210, then out to connecting fill channels 220 which deliver the sample to the well 110 (again at an inclined angle, providing gravity resistance to debris uptake).

The sample wells which receive the fluid from the second distribution through-channel circuit, like the sample wells which receive the fluid through the (front-planar) first distribution channel, also have bubble traps 170 associated with them, in the same general above-well configuration.

The biocard 100 therefore includes four rows by eight columns of sample wells built up by connecting channels through the first and second distribution channels. This provides a set of 32 sample wells. In addition, another contiguous set of samples wells, making up the remaining 32 wells for the total of 64, is also deployed along the bottom of the card body using through-channels.

More specifically, a third distribution channel 230 is in fluid connection with intake port 120, but traces a generally vertical path downward from the port to a third distribution through-channel 240, located at a lower right section of the card 100. Third distribution channel 230 and its corresponding third distribution through-channel 240 have slightly larger cross sections than the first two distribution channels and their through-channels 210, to accommodate larger fluid flow to a greater total number of destination wells (32, versus 8 and 24 wells, respectively).

The fluid flows down through the third distribution channel 230, into third distribution through-channel 240, and then splits into two subchannels. The first subchannel 250 on third distribution channel 230, located on the rear of card 100, is a widthwise channel extending along the lower base of the card, having a cross-section of approximately 0.2–0.3 mm$^2$. Rising up from first subchannel 250 are another set of triplet legs 260, which generally resemble first triplet 200 but which extend upward from first subchannel 230, rather than downward.

However, triplet legs 260 perform the same basic function, delivering the fluid to another set of through-channels 270, identical to through-channels 210. Through-channels 270 in turn lead through the card body, that is, to the front of the card, to connecting fill channels 280, which are generally short concave links (which may be kinked) to respective additional sample wells 110. Fill channels 280 likewise enter the sample wells 110 at an inclined angle, from above.

The last fluid flow path is second subchannel 290, leading off of third distribution through-channel 240 along the front of card 100, in a generally horizontal or widthwise manner. Second subchannel 290 is connected to the last (eighth), bottom row of eighth sample wells 110 by another set of vertical connecting conduits 300, single conduits connecting to single wells. Conduits 300 are generally dog-legged in structure, enter the well at a slightly inclined angle, and the associated wells each also include an associated bubble trap 170.

It may thus be seen that through the use of through-channels penetrating the card body 110, along with carefully distributed links through a plurality of distribution channels, in the invention valuable surface area is freed up on the card, by allowing the necessary connecting channels to be split up between the front and rear surfaces of the card.

The fluid flow paths thoroughly dispersed over card 100, including both front and rear surfaces, also result in a longer total linear travel of the flowing fluid tha conventional cards. This leads to the significant advantage that the possibility of inter-well contamination is reduced. The well-to-well distance in fact in the illustrated embodiment comes to approximately 35 mm, significantly more than the 12 mm or so on many older card designs.

The inventors have also observed that the rate of inter-well contamination varies with the square of the linear distance, so the elongated fluid paths significantly enhance the integrity of readings on the card. Contamination itself is a function of sample mixing (density of solution failing out of wells) and liquid molecular diffusion, both of which are discouraged by the relatively fine channel cross-sections in many sections of the overall fluid circuit, as well as overall path length.

The contamination rate is also reduced by the fact that the volume of the channels along the fluid circuit varies slightly along the overall circuit travelled by a given sample. That is, the through-channels, the three main distribution channels and other segments of the paths have cross-sectional areas which, although all relatively fine, may differ slightly. The change in volume over the path tends to retard the progression of contamination, as do dog-legged or kinked sections of connecting conduits.

All these structural adaptations cooperate in reducing the rate of inter-well contamination in the biocard 100. The inventors have, as one indication of contamination management, measured the time required for test dye to infiltrate a neighboring well in conventional biocards and the card of the invention. Contamination in a conventional, low-capacity, non-through-body card has been observed in approximately 24 hours. In the biocard of the invention under similar conditions, in contrast, the contamination time has been observed at 16–18 hours.

Besides contamination kinematics, the upper-placed bubble traps 170 also more efficiently scrub the sample wells 110 of gas bubbles which form after the sample injection. Samples are typically injected as noted by evacuating the card, introducing fluid at the intake and then releasing the vacuum pull, so that the whole fluid circuitry returns to atmospheric pressure. Vacuum filling of the card may typically be done over a period of 3–60 seconds, slower rates helping to reduce the tendency of bubbles to form. Those bubbles can ruin sample readings, so reducing them results in a smoother, more efficient, higher-capacity yet more reliable biocard.

In addition, the improved fluid circuitry of biocard 100, including full-radius fill and other channels, generally narrower channels than older card designs, width-variation and other features result in a high capture percentage of sample intake actually reaching the sample wells 110, which the inventors have calculated at as high as 90–95%. This compares with a capture percent in the 80s for older card designs.

For mechanical interaction with the automated reading machine, biocard 100 may also be provided with a series of sensor stop holes 310, located along the bottommost edge of the card. Sensor stop holes 310, illustrated as regularly spaced, rectangular through-holes, permit associated photodetectors to detect when a biocard 100 mounted in a reading machine has come into proper alignment for optical reading. The sensor stop holes 310 are arranged in vertical register with the vertical columns of wells 110, so that the optical detection of the stop hole 310 corresponds exactly to positioning of the sample wells 110 before optical reading devices. Older biocards have been aligned by sensor holes which are formed not integrally with the card itself, but in carriages or other supports which are attached to the card at some point in the reading process, as for instance disclosed in U.S. Pat. No. 4,118,280. These structures have however been prone to time-consuming maintenance, particularly requiring the mechanical calibration and lining up of the carriage with the cards, and photodetectors. Integral sensor stop holes 310 eliminate that type of difficulty.

The biocard 100 of the invention is formed in the illustrated embodiment, as shown in FIG. 7, with a mold parting line 320 which is formed most of the way down into a sample well 110, toward the bottom of the card as opposing mold dies meet during manufacture. Older card designs often had the mold parting line, which forms a tiny lip in a fluid cavity, at an upper point (above midway) of the card. The upper mold parting lines could tend to induce annular bubble rings to form during filling, as well as reduce the efficiency of drying of antibiotics or other material during manufacturing. The use of a downward offset mold parting line 320 avoids these difficulties, as well as improving the efficiency of chemical or antibiotic dehydration during incubation, and may act as a slight aperture during light and fluorescence reading operations. As illustrated in FIG. 7, the walls of the sample well, and other features, are usually formed at a slight angle or incline (typically 1–4°), as an artifact of conventional molding processes in which separating the molded part from opposing molding pieces is made easier with slight surface inclinations. The shifting of the mold parting line 320 to the bottom area of biocard 100 likewise results in a smaller inclined (roughly speaking, trapezoidal) area in the bottom of the sample well which can tend to trap material, slightly.

Another advantage of biocard 100 of the invention is that patient sample and other markings are not introduced directly on the card itself, in pre-formed segments, as for example shown in aforementioned U.S. Pat. No. 4,116,775 and others. Those on-card stipplings and markings can contribute to debris, mishandling and other problems. In the invention, instead, the card may be provided with bar-coding or other data markings by adhesive media, but markings or pre-formed information segments are not necessary (though some could be imprinted if desired) and debris, mishandling, loss of surface area and other problems can be avoided.

Biocard 100 furthermore includes, at the lower left corner of the card as illustrated in FIG. 1, a tapered bezel edge 330. Tapered bezel edge 330 provides an inclined surface for easier insertion of biocard 100 into, carrousels or cassettes, into slots or bins for card reading, and other loading points in the processing of the card. Tapered bezel edge 330 provides a gently inclined surface, which relieves the need for tight tolerances during loading operations.

Biocard 100 also includes a lower rail 360 and an upper rail 370, which are slight structural "bulges" at along the top and bottom areas of the card to reinforce the strength and enhance handling and loading of the biocard 100. The extra width of lower and upper rails 360 and 370 also exceeds the thickness of sealing material, such as adhesive tape, that is affixed to the front and back surfaces of biocard 100 for sealing during manufacture and impregnation with reagents. The raised rails therefore protect that tape, especially edges from peeling, during the making of the biocard 100, as well as during handling of the card, including during reading operations.

Upper rail 370 may have serrations 390 formed along its top edge, to provide greater friction when biocard 100 is transported in card reading machines or otherwise using belt drive mechanisms. Lower card rail 360 may also have formed in it reduction cavities 380, which are small elongated depressions which reduce the material, weight and expense of the card by carving out space where extra material is not necessary in the reinforcing rail 360.

Figure 2:
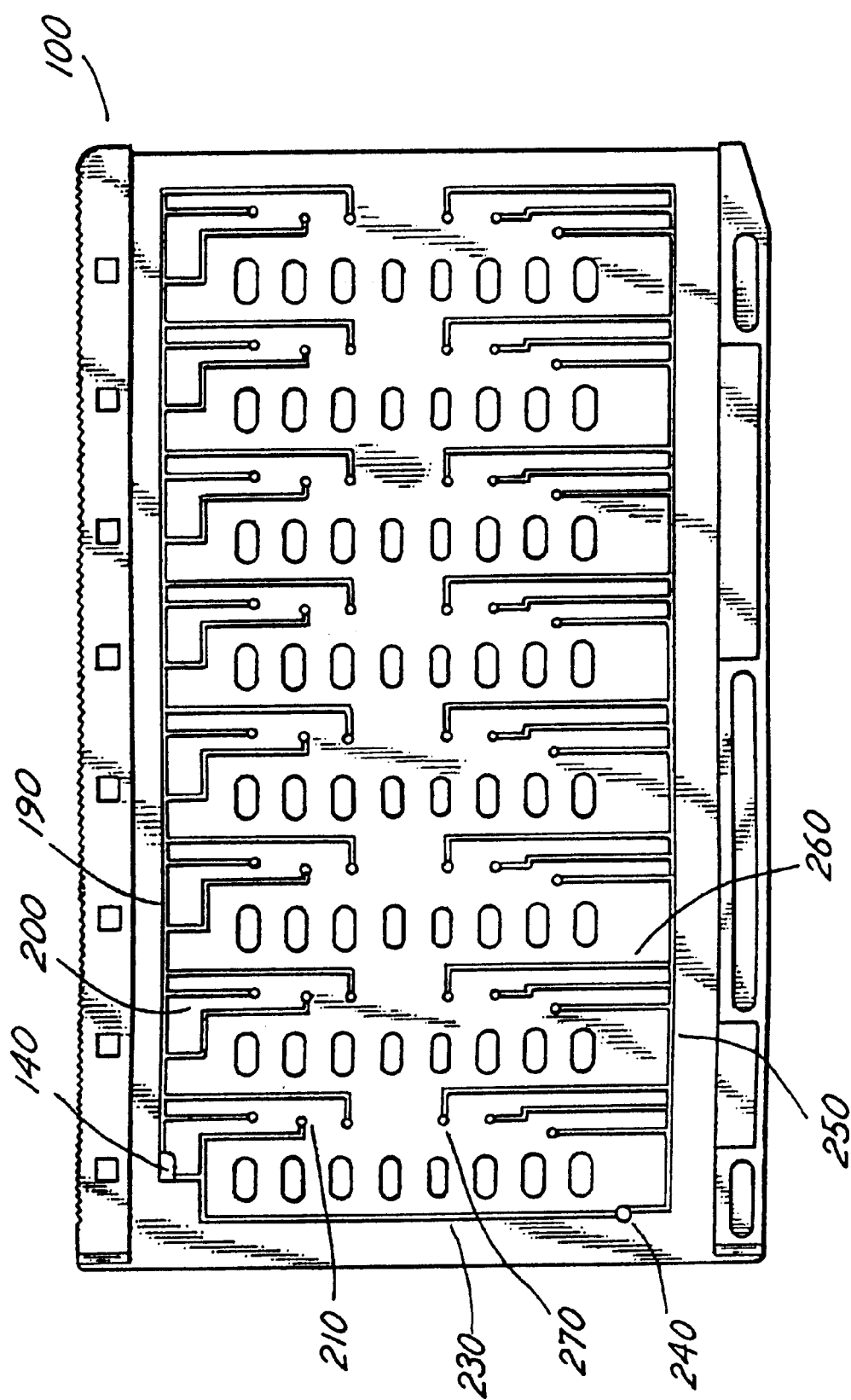
FIG. 2 illustrates the improved biocard according to the invention, in a back planar view.
Figure 3:
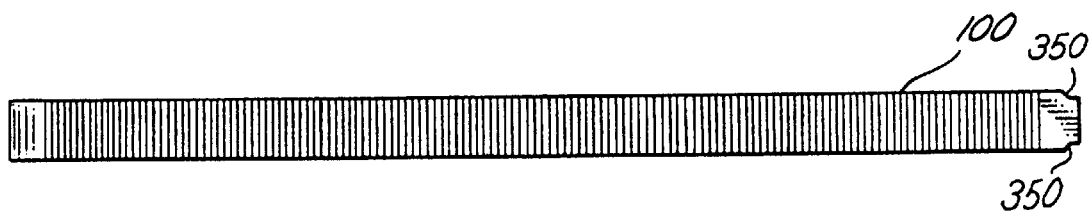
FIG. 3 illustrates the improved biocard according to the invention, in a top edge view.
Figure 4:
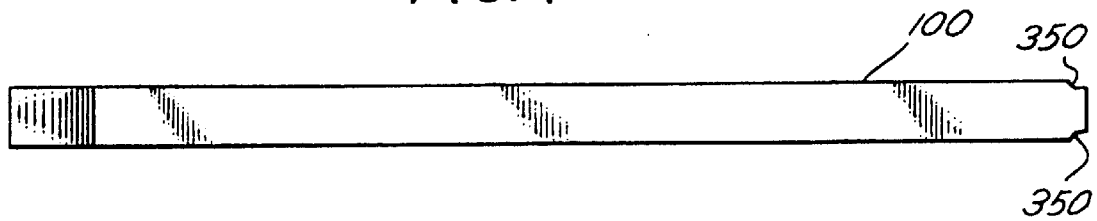
FIG. 4 illustrates the improved biocard according to the invention, in a bottom edge view.
Figure 5:
FIG. 5 illustrates the improved biocard according to the invention, in a side edge view.
Figure 6:
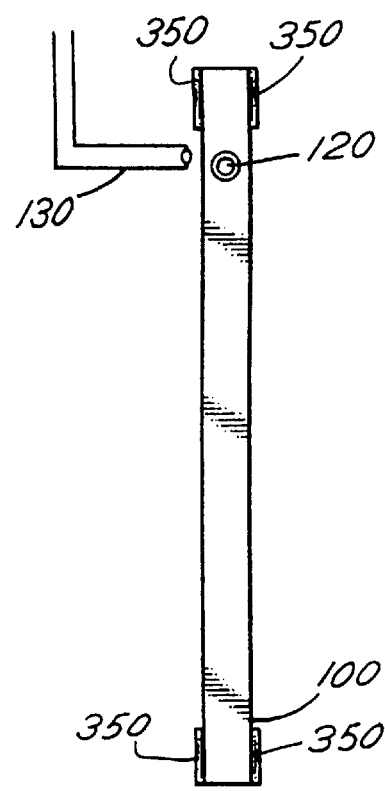
FIG. 6 illustrates the improved biocard according to the invention, in an opposite side edge view.

In terms of sealing of biocard 100 to contain reagents and other material, it has been noted that sealing tapes are typically used to seal flush against biocard 100 from either side, with rail protection. Biocard 100 also includes a leading lip 340 on lower card rail 360, and on upper card rail 370 which projects slightly over the leading edge of the card. Conversely, at the opposite end of the biocard 100 there is a trailing truncation 350 in both rails. This structure permits sealing tape to be applied in the card preparation process in a continuous manner, with card after card having tape applied, then the tape cut between successive cards without the tape from successive cards getting stuck together. The leading lip 340 and trailing truncation 350 provides a clearance to separate cards and their applied tape, which may be cut at the trailing truncation 350 and wrapped back around the card edge, for increased security against interference between abutting cards. Thus, the trailing truncation or slanted ramp feature 350 ends slightly inward from the extreme edge of the ends of the card, as shown in FIGS. 1 and 2 to define a portion of the card surface or "shelf portion" between the ends of the ramps 350 and the extreme edge of the card 100, extending across the width of the card 100. This shelf portion provides a cutting surface for a blade cutting the tape applied to the card. Further, the ramp 350 facilitates the stacking of multiple test sample cards without scuffing of the sealant tape applied to said cards, by allowing the ramps to slide over each other during a stacking motion with the raised rails preventing scuffing of the tape.

The foregoing description of the improved biocard of the invention is illustrative, and variations on certain aspects of the inventive system will occur to persons skilled in the art. The scope of the invention is accordingly intended to be limited only by the following claims.

We claim:

1. A test sample card comprising a rectangular card body having a first side portion, said card body moved relative to an optical system in a direction of travel parallel to said first side portion, said card body defining a plurality of sample wells arranged in an array on said card body, with all of said wells defined by said card body having a well length defining a major axis and a well width defining a minor axis, with said well length greater than said well width thereby providing an elongate well, wherein all of said wells defined by said card body are all substantially the same size and wherein all of said wells are arranged in said card body such that said major axis of said wells are oriented substantially parallel to said first side portion of said card body and thereby parallel to said direction of travel.

2. The test sample card of claim 1, wherein said wells are arranged in an array of a plurality of rows and columns of wells on said card body, with each of said wells in each of said columns of wells arranged in a manner such that said major axis of said wells is arranged in said card body substantially parallel to said first side portion of said card body.

3. The test sample card of claim 1, wherein said card body further comprises a top surface, a bottom surface, a sample entry port, and a fluid distribution channel network disposed in both said top surface and said bottom surface, said fluid channel network operatively connecting said sample entry port to said wells.

4. The test sample card of claim 1, wherein said card further comprises a first edge portion adjacent to said first side portion, a first end, a second side portion opposite said first side portion and a second edge portion adjacent to said second side portion, and wherein said first edge portion comprises a knurled texture area applied to said first edge portion of said card body facilitating the movement of said test sample card, and said second edge portion further comprises a tapered planar corner feature at the intersection of said second edge portion and said first end of said card.

5. A test sample card comprising a rectangular card body having a first side portion, said card body moved relative to an optical system in a direction of travel parallel to said first side portion, said card body defining a plurality of sample wells arranged in an array of a plurality of rows and columns of wells on said card body, said wells having a well length defining a major axis and a well width defining a minor axis, with said well length greater than said well width thereby providing an elongate well, wherein each of said wells in said columns of wells are arranged in a manner such that said major axis of said wells is arranged in said card body substantially parallel to said first side portion of said card body; and wherein said card further comprises a first edge portion adjacent to said first side portion and a knurled texture area applied to said first edge portion of said card body facilitating the movement of said test sample card.

6. The test sample card of claim 5, wherein said card further comprises a first end, a second side portion opposite said first side portion and a second edge portion adjacent to said second side portion, and wherein said second edge portion further comprises a tapered planar corner feature at the intersection of said second edge portion and said first end of said card.

* * * * *